United States Patent
Okabe

(10) Patent No.: US 11,412,919 B2
(45) Date of Patent: Aug. 16, 2022

(54) MEDICAL OBSERVATION SYSTEM

(71) Applicant: Sony Olympus Medical Solutions Inc., Tokyo (JP)

(72) Inventor: Yasuhiro Okabe, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 131 days.

(21) Appl. No.: 16/802,602

(22) Filed: Feb. 27, 2020

(65) Prior Publication Data
US 2020/0297195 A1  Sep. 24, 2020

(30) Foreign Application Priority Data

Mar. 19, 2019 (JP) .............................. JP2019-051416
Jan. 10, 2020 (JP) .............................. JP2020-003151

(51) Int. Cl.
*A61B 1/00* (2006.01)
*A61B 1/06* (2006.01)

(52) U.S. Cl.
CPC ...... *A61B 1/00149* (2013.01); *A61B 1/00009* (2013.01); *A61B 1/00117* (2013.01); *A61B 1/00195* (2013.01); *A61B 1/06* (2013.01)

(58) Field of Classification Search
CPC . A61B 34/30; A61B 1/00149; A61B 1/00117; A61B 1/00195; A61B 1/00009; A61B 1/06; A61B 90/25; A61B 2090/306; A61B 2090/371; A61B 2090/508; A61B 2090/502; A61B 1/0669; G02B 7/001; G02B 21/0012

USPC ......................................................... 600/102
See application file for complete search history.

(56) References Cited

U.S. PATENT DOCUMENTS 5,048,941 A * 9/1991 Hamada ............. G02B 21/0012
                                                     359/368
2005/0057800 A1* 3/2005 Obrebski ............... A61B 90/50
                                                     359/385

FOREIGN PATENT DOCUMENTS

JP      2016-059499 A       4/2016
WO  WO-2017029906 A1 *  2/2017 ............. G02B 21/24

* cited by examiner

*Primary Examiner* — Michael J Carey
*Assistant Examiner* — Christen A. Sharpless
(74) *Attorney, Agent, or Firm* — Xsensus, LLP

(57) ABSTRACT

A medical observation system includes: a microscope; a support including a first joint configured to hold the microscope such that the microscope is rotatable about a first axis parallel to an optical axis of the microscope; and a first arm configured to hold the first joint and extend in a direction different from a direction of the optical axis of the microscope; a light guide cable inserted in the support and configured to guide illumination light to the microscope; and a binder configured to bind the light guide cable, wherein at least a part of the light guide cable is arranged along the first axis in a first section, the light guide cable extends in a direction different from the first axis in a second section, and the binder is configured to bind the light guide cable in the second section.

13 Claims, 5 Drawing Sheets

MEDICAL OBSERVATION SYSTEM

This application claims priority from Japanese Application No. 2019-051416, filed on Mar. 19, 2019, and Japanese Application No. 2020-003151, filed on Jan. 10, 2020, the contents of which are incorporated by reference herein in its entirety.

BACKGROUND

The present disclosure relates to a medical observation system.

In the related art, as a medical observation system for observing a micro region in a brain, a heart, or the like of a patient as an observed body when performing surgery on the micro region, an optical microscope system that includes a microscope unit with an imaging sensor and a magnification optical system for enlarging the micro region has been known (for example, see Japanese Laid-open Patent Publication No. 2016-59499). When performing surgery using the microscope system as described above, an operator (user), such as a doctor, moves the microscope unit to a desired position and performs the surgery while observing a surgical site.

In the microscope system disclosed in Japanese Laid-open Patent Publication No. 2016-59499, the microscope unit has a cylindrical shape, and a cable group including a plurality of thin coaxial cables that are connected to the imaging sensor and including a light guide that guides illumination light to a distal end of the microscope unit are inserted in the microscope unit. In Japanese Laid-open Patent Publication No. 2016-59499, the cable group connected to the imaging sensor is bound by two binding units that are arranged on a rotation axis of the microscope unit.

SUMMARY

If the cable group or the like is bound on the rotation axis as in Japanese Laid-open Patent Publication No. 2016-59499, the cable group is twisted when the microscope unit rotates. When the cable group is twisted, the cable group is pulled between the binding units, so that the cable group may interfere with other components, and the cables and the components may be damaged. To cope with this, to prevent the interference with the other components, it may be possible to ensure a cable arrangement space corresponding to an amount of pulling in a height direction (in this example, in a rotation axis direction) of the microscope unit inside the microscope unit; however, a size of the microscope unit or the like is increased by a size of the space, which is a problem.

According to the present disclosure, there is provided a medical observation system including: a microscope; a support including a first joint configured to hold the microscope such that the microscope is rotatable about a first axis parallel to an optical axis of the microscope; and a first arm configured to hold the first joint and extend in a direction different from a direction of the optical axis of the microscope; a light guide cable inserted in the support and configured to guide illumination light to the microscope; and a binder configured to bind the light guide cable, wherein at least a part of the light guide cable is arranged along the first axis in a first section, the light guide cable extends in a direction different from the first axis in a second section, and the binder is configured to bind the light guide cable in the second section.

DETAILED DESCRIPTION

An embodiment will be described below with reference to the accompanying drawings. The drawings are schematic and different drawings may include a portion that has different dimensional relations or ratios.

Figure 1:
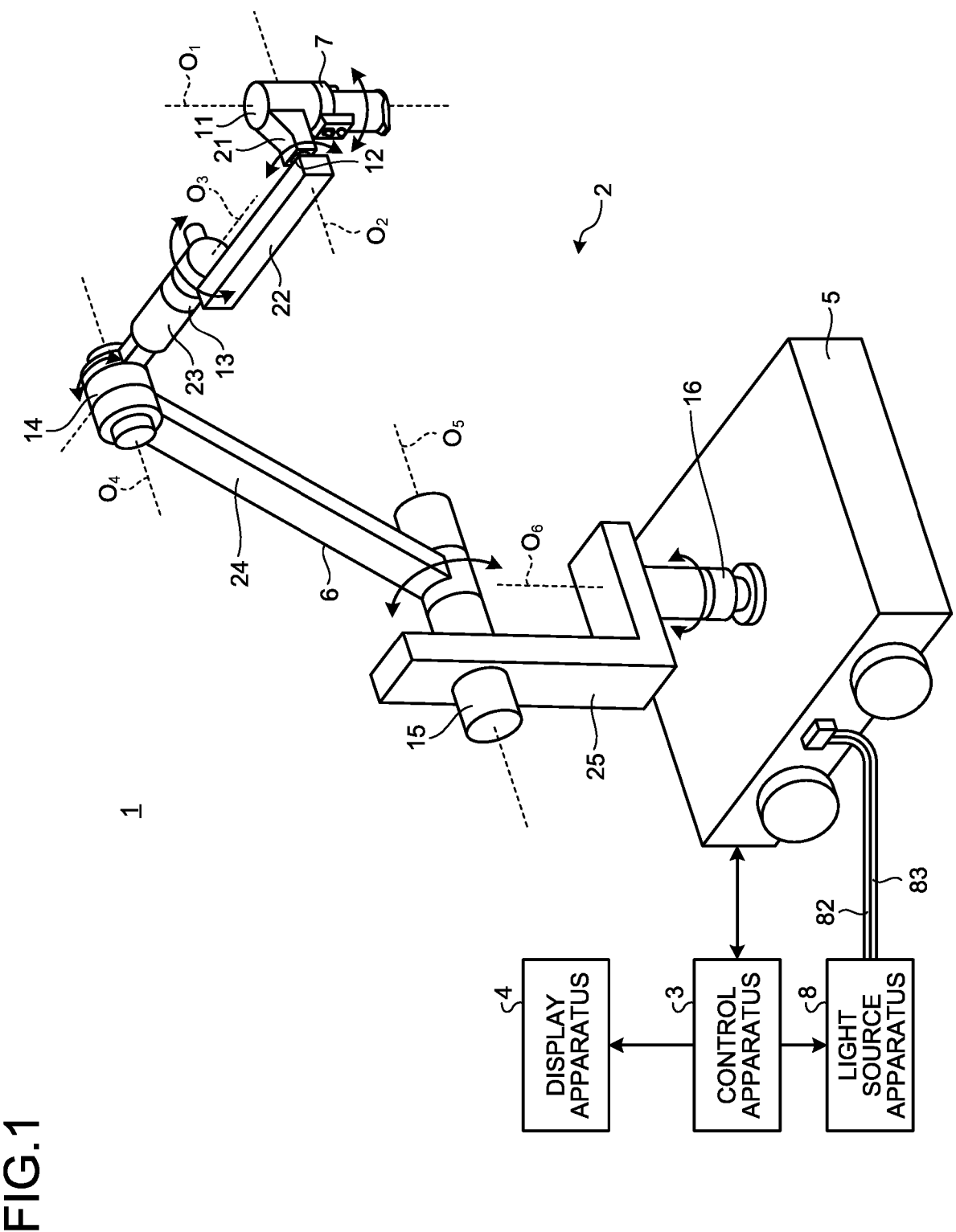
FIG. 1 is a perspective view illustrating an external configuration of a medical observation system according to an embodiment.

FIG. 1 is a diagram illustrating a configuration of a medical observation system according to an embodiment. A medical observation system 1 illustrated in FIG. 1 includes a medical observation apparatus (hereinafter, referred to as an observation apparatus) 2 having a function as a microscope that captures an image of a microstructure of an observed body in an enlarged manner, a control apparatus 3 that integrally controls operation of the medical observation system 1, and a display apparatus 4 that displays an image captured by the observation apparatus 2.

The observation apparatus 2 includes a base unit 5 that is movable on a floor surface, a support unit 6 that is supported by the base unit 5, and a columnar microscope unit 7 that is arranged at a distal end of the support unit 6 and captures an image of a micro region of an observed body in an enlarged manner. Further, a light source apparatus 8 that supplies illumination light to the observation apparatus 2 via light guide cables 82 and 83 that are configured with optical fiber or the like is connected to the observation apparatus 2.

In the observation apparatus 2, for example, a cable group including a transmission cable, which includes a signal cable (thin coaxial cable) for transmitting signals between the control unit and the microscope unit 7, and including a light guide cable for guiding illumination light from the light source apparatus 8 to the microscope unit 7 is arranged from the base unit 5 to the microscope unit 7. The cable group is arranged along the support unit 6. The thin coaxial cable is a cable with a smaller diameter than a diameter of the light guide cable.

The support unit 6 includes a first joint part 11, a first arm part 21, a second joint part 12, a second arm part 22, a third joint part 13, a third arm part 23, a fourth joint part 14, a fourth arm part 24, a fifth joint part 15, a fifth arm part 25, and a sixth joint part 16.

The support unit 6 includes four sets, each including two arm parts and a joint part that connects one (distal end side) of the two arm parts to the other one (proximal end side) of the two arm parts in a rotatable manner. Specifically, the four sets are as follows: (the first arm part 21, the second joint part 12, and the second arm part 22), (the second arm part 22, the third joint part 13, and the third arm part 23), (the third arm part 23, the fourth joint part 14, and the fourth arm part 24), and (the fourth arm part 24, the fifth joint part 15, and the fifth arm part 25).

The first joint part 11 holds the microscope unit 7 on a distal end side such that the microscope unit 7 may rotate, and is held by the first arm part 21 such that a proximal end side of the first joint part 11 is fixed to a distal end portion of the first arm part 21. The first joint part 11 has a cylindrical shape and holds the microscope unit 7 such that the microscope unit 7 may rotate about a first axis $O_1$ that is a central axis in a height direction. The first arm part 21 has a shape that extends from a side surface of the first joint part 11 in a direction perpendicular to the first axis $O_1$. A detailed configuration of the first joint part 11 will be described later. Meanwhile, it is preferable that the first joint part 11 allows the microscope unit 7 to rotate by 360° or larger about the first axis $O_1$. By allowing the rotation by 360° or larger, it is possible to align an imaging direction of an imaging unit 72 with an observation direction of the operator in accordance with an operator's standing position regardless of a position at which the operator stands relative to the observation apparatus 2. It is more preferable to cause the first joint part 11 to allow rotation by 400° or larger. If a rotation angle is set to 400° or larger, it becomes possible to adjust the rotation angle from any rotation angle without limiting the rotation direction.

The second joint part 12 holds the first arm part 21 on a distal end side such that the first arm part 21 may rotate, and is held by the second arm part 22 such that a proximal end side of the second joint part 12 is fixed to a distal end portion of the second arm part 22. The second joint part 12 has a cylindrical shape and holds the first arm part 21 such that the first arm part 21 may rotate about a second axis $O_2$ that is a central axis in a height direction and that is an axis perpendicular to the first axis $O_1$. The second arm part 22 has an approximately L-shape, and is connected to the second joint part 12 at an end portion of a vertical portion of the L-shape.

The third joint part 13 holds a horizontal portion of the L-shape of the second arm part 22 on a distal end side such that the second arm part 22 may rotate, and is held by the third arm part 23 such that a proximal end side of the third joint part 13 is fixed to a distal end portion of the third arm part 23. The third joint part 13 has a cylindrical shape and holds the second arm part 22 such that the second arm part 22 may rotate about a third axis $O_3$ that is a central axis in a height direction, that is an axis perpendicular to the second axis $O_2$, and that is an axis parallel to a direction along which the second arm part 22 extends. A distal end side of the third arm part 23 is formed in a cylinder, and a hole portion is formed on a proximal end side of the third arm part 23 such that the hole portion penetrates in a direction perpendicular to a height direction of the cylinder provided on the distal end side. The third joint part 13 is held by the fourth joint part 14 via the hole portion such that the third joint part 13 may rotate.

The fourth joint part 14 holds the third arm part 23 on a distal end side such that the third arm part 23 may rotate, and is held by the fourth arm part 24 such that a proximal end side of the fourth joint part 14 is fixed to the fourth arm part 24. The fourth joint part 14 has a cylindrical shape and holds the third arm part 23 such that the third arm part 23 may rotate about a fourth axis $O_4$ that is a central axis in a height direction and that is an axis perpendicular to the third axis $O_3$.

The fifth joint part 15 holds the fourth arm part 24 on a distal end side such that the fourth arm part 24 may rotate, and a proximal end side of the fifth joint part 15 is fixedly mounted on the fifth arm part 25. The fifth joint part 15 has a cylindrical shape and holds the fourth arm part 24 such that the fourth arm part 24 may rotate about a fifth axis $O_5$ that is a central axis in a height direction and that is an axis parallel to the fourth axis $O_4$. The fifth arm part 25 includes an L-shaped portion and a bar-shaped portion that extends downward from a horizontal portion of the L-shaped portion. The proximal end side of the fifth joint part 15 is mounted on an end portion of a vertical portion of the L-shaped portion of the fifth arm part 25.

The sixth joint part 16 holds the fifth arm part 25 on a distal end side such that the fifth arm part 25 may rotate, and a proximal end side of the sixth joint part 16 is fixedly mounted on an upper surface of the base unit 5. The sixth joint part 16 has a cylindrical shape and holds the fifth arm part 25 such that the fifth arm part 25 may rotate about a sixth axis $O_6$ that is a central axis in a height direction and that is an axis perpendicular to the fifth axis $O_5$. A proximal end portion of the bar-shaped portion of the fifth arm part 25 is mounted on a distal end side of the sixth joint part 16.

The support unit 6 configured as described above realizes movement with a total of six kinds of flexibility, such as three kinds of translational flexibility and three kinds of rotational flexibility, in the microscope unit 7.

The first joint part 11 to the sixth joint part 16 include electromagnetic brakes that inhibit rotation of the microscope unit 7 and the first arm part 21 to the fifth arm part 25. Each of the electromagnetic brakes is released when an arm operation switch 73 (to be described later) arranged in the microscope unit 7 is pressed, and allows the microscope unit 7 and the first arm part 21 to the fifth arm part 25 to rotate. It may be possible to adopt air brakes instead of the electromagnetic brakes.

Figure 2:
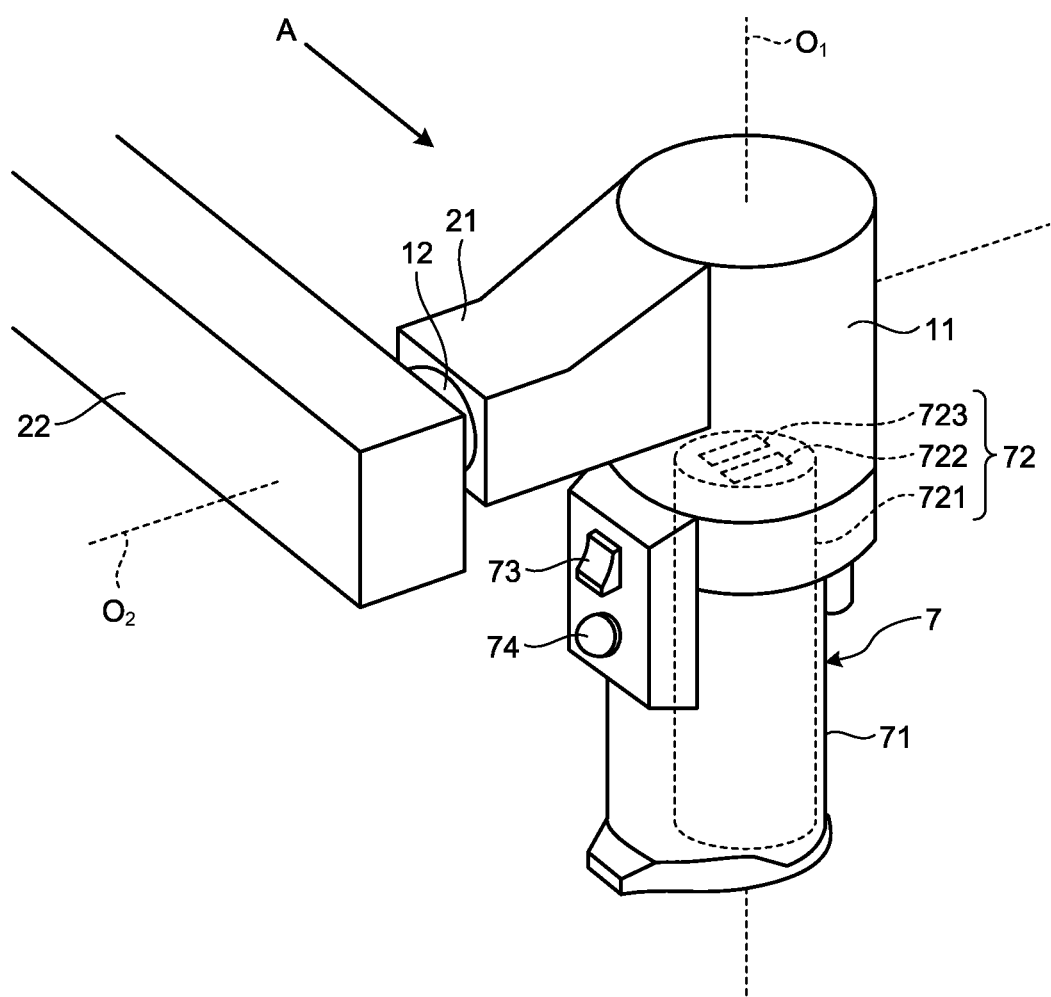
FIG. 2 is an enlarged perspective view illustrating configurations a microscope unit and peripheral units of the microscope unit in the medical observation apparatus according to the embodiment.
Figure 3:
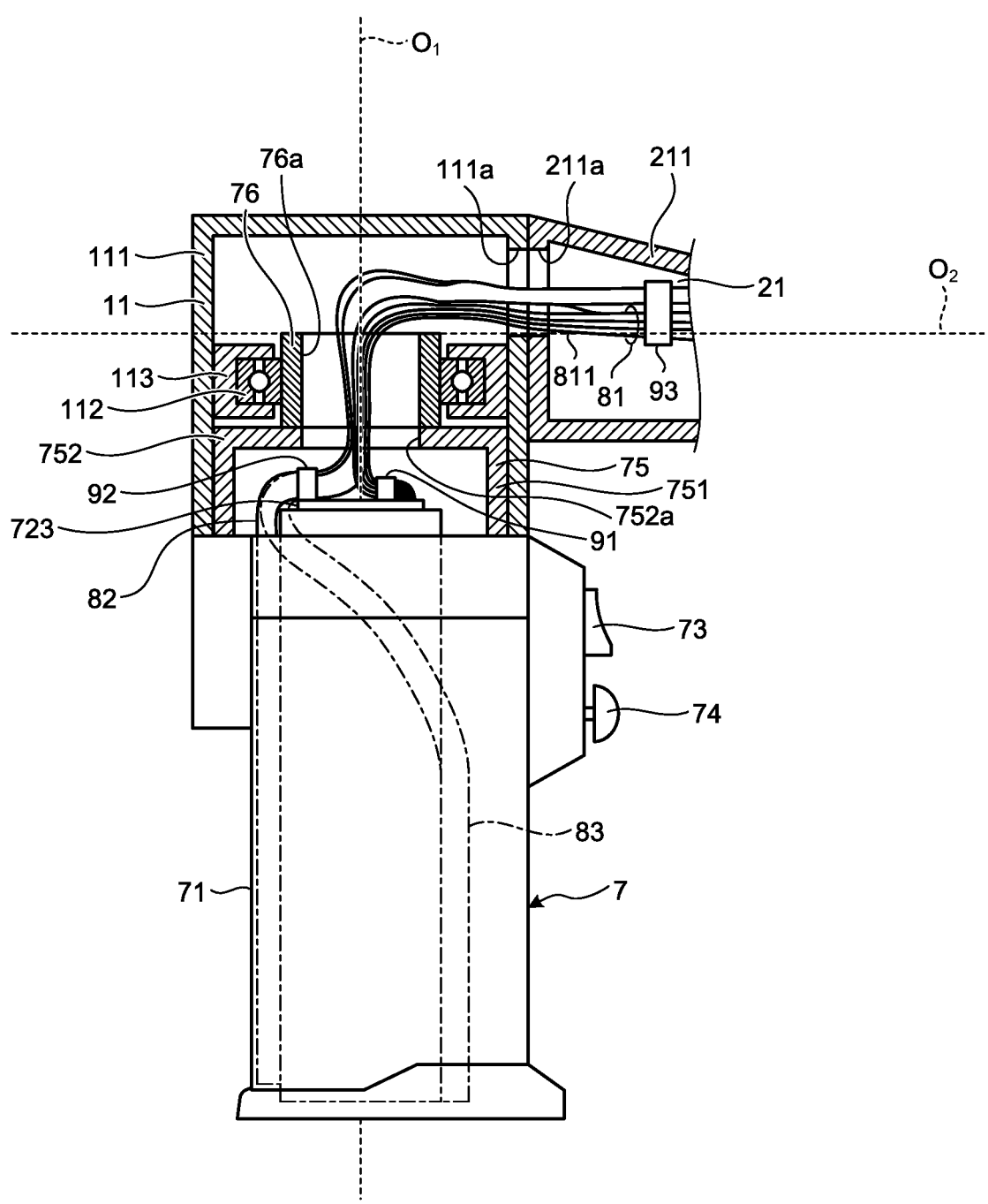
FIG. 3 is a partial cross-sectional view, viewed from a direction of an arrow A in FIG. 2.

FIG. 2 is an enlarged perspective view illustrating configurations of the microscope unit 7 and peripheral units of the microscope unit 7 in the observation apparatus 2. FIG. 3 is a partial cross-sectional view, viewed from a direction of an arrow A in FIG. 2. The configuration of the microscope unit 7 will be described below with reference to FIG. 2 and FIG. 3.

The microscope unit 7 includes a tubular part 71 having a cylindrical shape, the imaging unit 72 that is arranged in a hollow part of the tubular part 71 and captures an image of an observed body in an enlarged manner, the arm operation switch 73 that receives input of operation for releasing the electromagnetic brakes of the first joint part 11 to the sixth joint part 16 and allowing each of the joint parts to rotate, a cross lever 74 capable of changing an enlargement magnification and a focal length to the observed body in the imaging unit 72, an upper cover 75 that is formed on a periphery of an upper part of the imaging unit 72 and fitted into the first joint part 11, and a hollow cylindrical shaft part 76 that extends from the upper cover 75 along the first axis $O_1$.

The tubular part 71 is formed in a cylinder with a smaller diameter than a diameter of the first joint part 11, and a cover glass (not illustrated) for protecting the imaging unit 72 is arranged on an opening surface of a lower end portion of the tubular part 71. The tubular part 71 need not always be formed in a cylindrical shape, but may be formed in a tubular shape whose cross section perpendicular to the height direction has an elliptical or polygonal shape.

The imaging unit 72 includes an optical system 721 that has a plurality of lenses arranged such that optical axes match the first axis $O_1$, that condenses light from the observed body, and that forms an image, and two imaging sensors 722 and 723 that receive the light condensed by the optical system 721, perform photoelectric conversion on the light, and generate imaging signals. In FIG. 2, only a tubular casing that houses the plurality of lenses of the optical system 721 is illustrated.

The optical system 721 is able to change an enlargement magnification of an image of the observed body and a focal length to the observed body in accordance with operation on the cross lever 74.

Each of the imaging sensors 722 and 723 is configured using a charge coupled device (CCD) or a complementary metal oxide semiconductor (CMOS). The imaging sensors 722 and 723 generate two imaging signals with disparities, as imaging signals for generating a three-dimensional image. The imaging signals are output, as digital signals, from the imaging sensors 722 and 723.

The arm operation switch 73 is a push-button switch. While a user is pressing the arm operation switch 73, the electromagnetic brakes of the first joint part 11 to the sixth joint part 16 are released. The arm operation switch 73 is arranged on a side surface opposite to a side surface that faces the user when the user operates the microscope unit 7, in other words, on the side surface that is located in the user's blind spot during operation of the microscope unit 7. The arm operation switch 73 constitutes a part of an operation input unit that receives input of operation on the observation apparatus 2.

The cross lever 74 may be operated along a height direction of the tubular part 71 and a circumferential direction perpendicular to the height direction. The cross lever 74 is arranged on a side surface of the tubular part 71 so as to be located below the arm operation switch 73 on the side surface along the height direction of the tubular part 71. The cross lever 74 also constitutes a part of the operation input unit that receives input of operation on the observation apparatus 2, similarly to the arm operation switch 73.

If the cross lever 74 is operated along the height direction of the tubular part 71 from the position as illustrated in FIG. 2, the enlargement magnification is changed, and, if the cross lever 74 is operated along the circumferential direction of the tubular part 71 from the position as illustrated in FIG. 2, the focal length to the observed body is changed. For example, if the cross lever 74 is moved upward along the height direction of the tubular part 71, the enlargement magnification increases, and if the cross lever 74 is moved downward along the height direction of the tubular part 71, the enlargement magnification decreases. Further, if the cross lever 74 is moved clockwise along the circumferential direction of the tubular part 71, the focal length to the observed body increases, and if the cross lever 74 is moved counterclockwise along the circumferential direction of the tubular part 71, the focal length to the observed body decreases. The moving directions and assignment of operation of the cross lever 74 are not limited to those as described above.

The upper cover 75 includes a cylindrical part 751 and a hollow disk part 752 that is arranged on an upper end portion of the cylindrical part 751 and that has the same diameter as a diameter of the cylindrical part 751. The cylindrical shaft part 76 that extends along the first axis $O_1$ and that has a hollow part 76a communicating with a hollow part 752a of the hollow disk part 752 is mounted on the hollow disk part 752.

Configurations of main parts of the first joint part 11 will be described below with reference to FIG. 3. The first joint part 11 includes an outer frame 111 which has an upper end portion formed in a bottomed cylindrical shape and in which the upper cover 75 of the microscope unit 7 is fitted along an inner periphery, a shaft support part 112 that supports the shaft part 76 of the microscope unit 7 such that the shaft part 76 may rotate, and a holder part 113 that is fixed to the outer frame 111 and that fixedly holds an outer periphery of the shaft support part 112. The outer frame 111 is fixedly connected to an outer frame 211 of the first arm part 21. A through hole 111a is formed in a portion connected to the outer frame 211 on the outer frame 111. The through hole 111a communicates with a through hole 211a formed in the outer frame 211. Meanwhile, in FIG. 3, illustration of configurations of the electromagnetic brakes and the like are omitted.

In the distal end portion of the observation apparatus 2, a height of the outer frame 111 is reduced to an amount that is needed to arrange the cable group, and the outer frame 211 is inclined; therefore, when the user operates the microscope unit 7, the distal end portion is less likely to appear in the visual field of the user. Therefore, by reducing a percentage of the distal end portion of the observation apparatus 2 in the visual field of the user, it is possible to prevent disturbance of the visual field of the user.

In the observation apparatus 2, the user is able to press the arm operation switch 73 and operate the support unit 6 while naturally holding the microscope unit 7. In particular, because the arm operation switch 73 is arranged on the side surface that is located in the user's blind spot among the side surfaces of the microscope unit 7 (the side surface opposite to the side surface that faces the user), the user is able to perform operation of continuously pressing the arm operation switch 73 and operation of pressing and releasing the arm operation switch 73 without feeling uncomfortable even when the user rotates or inclines the microscope unit 7 while holding the microscope unit 7 in the user's hand.

Further, in the observation apparatus 2, it is not necessary to separately arrange a grip portion equipped with the arm operation switch 73, so that it is possible to configure the microscope unit 7 with a small size and it is possible to adequately ensure the field of view of the user.

Furthermore, in the observation apparatus 2, the user is allowed to hold the periphery of the microscope unit 7 in the user's hand, and therefore, the user is able to intuitively recognize a position of the optical axis of the optical system 721, in other words, a direction of an imaging visual field, and is able to easily move the microscope unit 7 to a desired position; thus, the operability is excellent.

A configuration for transmitting the imaging signals output by the imaging unit 72 will be described below with reference to FIG. 3. A plurality of thin coaxial cables 811 as a transmission means for transmitting the imaging signals are extended from the imaging sensors 722 and 723, and constitute, as a whole, a cable group 81. The cable group 81 passes through the hollow part 76a of the shaft part 76. The cable group 81 is bound by binding units 91 and 93 on outer portions at both end sides of the shaft part 76. Therefore, the cable group 81 is in a bundle form between the binding unit 91 and the binding unit 93. A part of a bundle portion of the cable group 81 is arranged along the first axis $O_1$ in the hollow part 76a. Further, the cable group 81 extends from the first joint part 11 to the first arm part 21 via the through hole 111a of the outer frame 111 and the through hole 211a of the outer frame 211. Here, the binding unit 92 corresponds to a second binding unit, and the binding unit 91 corresponds to a third binding unit.

Furthermore, two light guide cables (the light guide cables 82 and 83) extend from the base unit 5 via the through hole 111a of the outer frame 111 and the through hole 211a of the outer frame 211, and pass through the hollow part 76a of the shaft part 76, similarly to the cable group 81. The light guide cables 82 and 83 are bound by the binding units 92 and 93 on the outer portions at both end sides of the shaft part 76. Therefore, parts of bound portions of the light guide cables 82 and 83 are arranged along the first axis $O_1$ in the hollow part 76a. Moreover, the light guide cables 82 and 83 extend to the distal end of the microscope unit 7 along the outer circumference of the imaging unit 72 via the binding unit 92. Illumination light guided by the light guide cables 82 and 83 is emitted from a distal end surface of the microscope unit 7 to outside in a direction of the first axis $O_1$, for example.

In the present embodiment, at least parts of the cable group 81 and the light guide cables 82 and 83 are arranged along the first axis $O_1$ in the hollow part 76a.

Furthermore, the binding unit 93 is arranged inside the first arm part 21, and binds the cable group 81 and the light guide cables 82 and 83 at a position separated from the first axis $O_1$. Meanwhile, the cable group 81 and the light guide cables 82 and 83 may be simply referred to as cables.

In this example, sizes of openings of the through holes 111a and 211a are larger than a length of a bundle of the cable group 81 and the light guide cables 82 and 83 in a circle direction. In other words, insertion positions of the cable group 81 and the light guide cables 82 and 83 in the through holes 111a and 211a are changeable.

Figure 4:
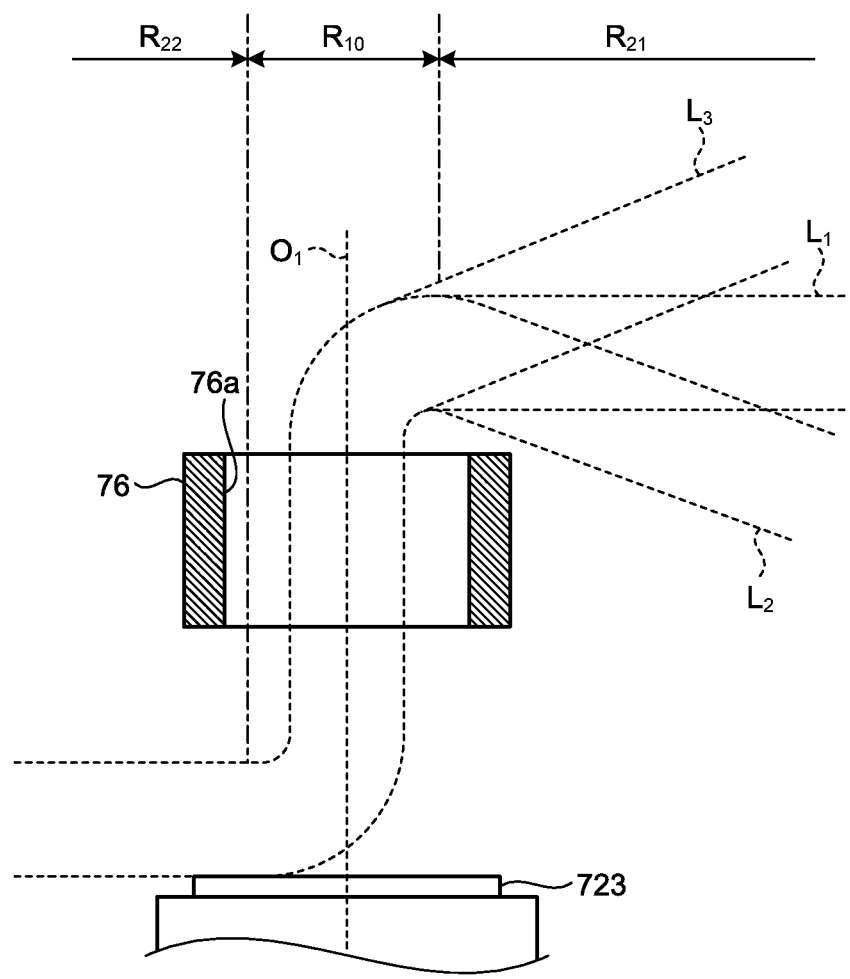
FIG. 4 is a diagram for explaining a binding position in the microscope unit of the medical observation apparatus according to the embodiment.

Bind positions of the cable group 81 and the light guide cables 82 and 83 by the binding units will be described below with reference to FIG. 4. FIG. 4 is a diagram for explaining the bind positions in the microscope unit of the medical observation apparatus according to the embodiment. In the present embodiment, each of the binding units (the binding units 91 to 93) is arranged in a portion that does not include the first axis $O_1$ in a cable arrangement path, e.g., in a certain portion that is extended from the hollow part 76a and located following a bent portion in the path. FIG. 4 illustrates an example of a path that may be taken by the light guide cables. For example, examples of a path of the light guide cable that enters the first joint part 11 from the base unit 5 side via the second joint part 12 to the sixth joint part 16 includes a path $L_1$ in which the light guide cable is bent in a direction perpendicular to an extending direction (the first axis $O_1$) and then enters the hollow part 76a, a path $L_2$ in which the light guide cable is bent at an acute angle with respect to the extending direction (the first axis $O_1$) and then enters the hollow part 76a, and a path $L_3$ in which the light guide cable is bent at an obtuse angle with respect to the extending direction (the first axis $O_1$) and then enters the hollow part 76a. The light guide cable passes through the hollow part 76a, and thereafter is bent so as to avoid the imaging sensors 722 and 723 (only the imaging sensor 723 is illustrated in FIGS. 3 and 4).

In the paths $L_1$ to $L_3$ as described above, the bind position located on an upstream side of the hollow part 76a is set in a second section $R_{21}$ in which the cable in each of the paths extends in a direction different from the first axis $O_1$ and which is separated from a first section $R_{10}$ in which at least a part of the cable is arranged along the first axis $O_1$ in each of the paths. The second section $R_{21}$ includes a part of the shaft part 76 and the first arm part 21. In contrast, the bind position located on a downstream side of the hollow part 76a is set in a third section $R_{22}$ in which the cable in each of the paths extends in a direction different from the first axis $O_1$ and which is separated from the first section $R_{10}$. In other words, the binding unit 93 is arranged on a path (second section) in which the cable is not arranged along the first axis $O_1$ and extends in a direction different from the direction of the first axis $O_1$. In the present embodiment, it is assumed that the binding unit 93 is arranged in the first arm part. Furthermore, the binding units 91 and 92 are arranged on paths in which the cables are not arranged along the first axis $O_1$ and extend in directions different from the direction of the first axis $O_1$, in a third section opposite to the second section across the first section.

Meanwhile, the second section $R_{21}$ and the third section $R_{22}$ are hollow radial regions about the first axis $O_1$ as a central axis. A hollow region in this example corresponds to the first section $R_{10}$. For example, the third section $R_{22}$ is a hollow radial region that is formed between the shaft part 76 and the image sensor 723.

Here, by arranging the binding unit 93 at the position separated from the first axis $O_1$, and providing the through holes 111a and 211a with the openings larger than the length of the bundle of the cable group 81 and the light guide cables 82 and 83 in the circle direction, it is possible to ensure a cable length corresponding to an amount of displacement that occurs when the light guide cables are pulled due to rotation of the microscope unit 7 and ensure a space that allows the displacement, so that it is possible to prevent interference between the cables and peripheral members. Therefore, it is preferable to increase the sizes of the openings of the through holes 111a and 211a, and arrange the binding unit 93 at a position separated from the first axis $O_1$. For example, the binding unit 93 is arranged at a position separated from the first axis O1 by a distance that is longer than a distance corresponding to a half of an inner diameter of the shaft part 76.

Meanwhile, it is preferable to set an inter-binding-unit distance between one end side (the binding unit 92) and the other end side (the binding unit 93) in the light guide cables 82 and 83 to a length longer than a length of an inter-binding-unit distance between one end side (the binding unit 91) and the other end side (the binding unit 93) in the cable group 81, in order to reduce a torsion torque. Furthermore, if the first joint part 11 is able to rotate the microscope unit 7 by 360° or larger, it is preferable to set a distance from the binding unit 92 to the binding unit 93 to be equal to or larger than four times of the inner diameter of the shaft part 76 (in this example, a diameter of the hollow part 76a) in which the cable group 81 is inserted, in order to prevent interference of the cable group 81. The "inter-binding-unit distance" in this example indicates a length extended between the binding units in a predetermined cable among the cables bound by the binding units. The predetermined cable is, for example, a cable in which a length between the binding units is maximum or minimum. Further, an average length of lengths between the binding units in a plurality of bound cable groups may be adopted.

Explanation of the configuration of the medical observation system 1 is continued below.

The control apparatus 3 receives an imaging signal output by the observation apparatus 2, performs predetermined signal processing on the imaging signal, and generates three-dimensional image data to be displayed. The control apparatus 3 is configured using a central processing unit (CPU), a read only memory (ROM), a random access memory (RAM), or the like. Meanwhile, the control apparatus 3 may be set inside the base unit 5 and integrated with the observation apparatus 2.

The display apparatus 4 receives, from the control apparatus 3, the three-dimensional image data generated by the control apparatus 3, and displays a three-dimensional image corresponding to the three-dimensional image data. The display apparatus 4 as described above includes a display panel made with liquid crystal or organic electro luminescence (EL).

Figure 5:
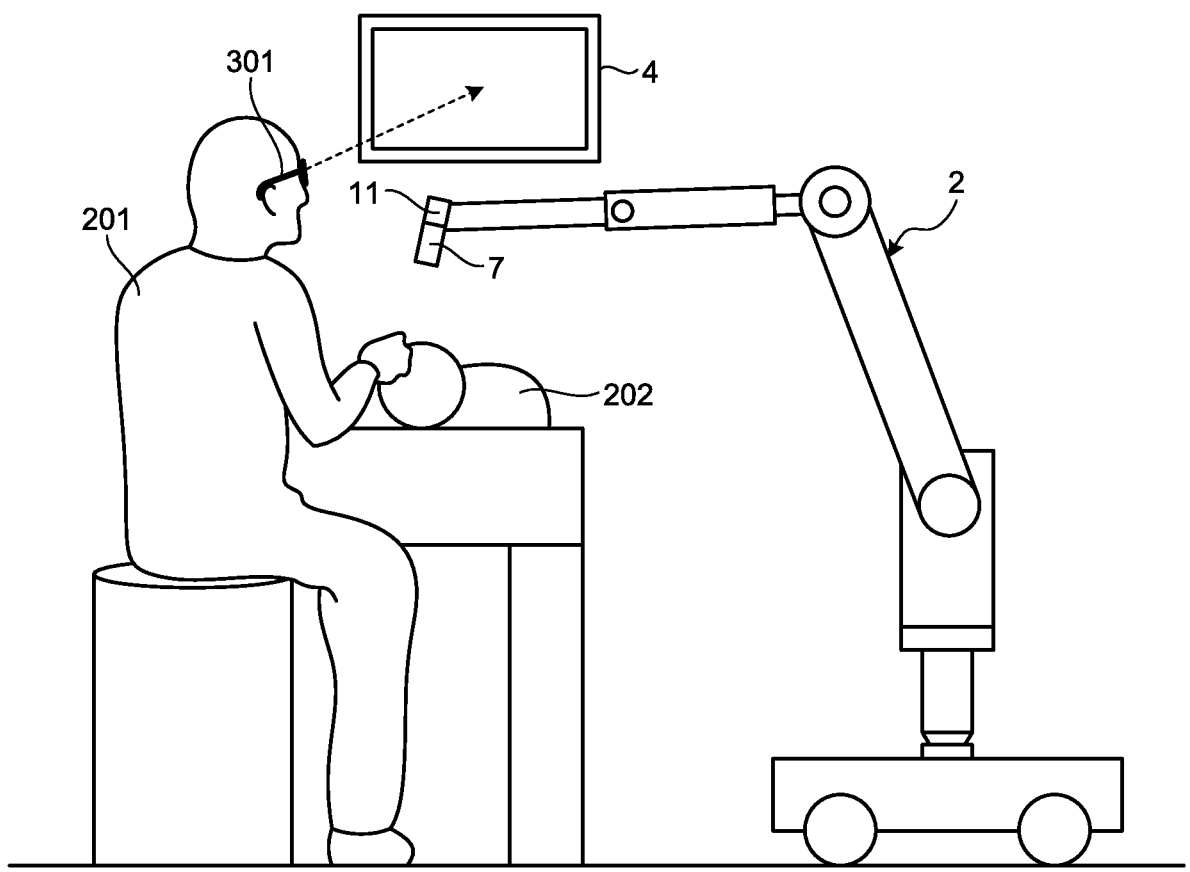
FIG. 5 is a diagram schematically illustrating a situation in which surgery is performed using the medical observation system according to the embodiment.

An outline of surgery that is performed using the medical observation system 1 configured as described above will be described below. FIG. 5 is a diagram schematically illustrating a situation in which surgery is performed using the medical observation system 1. Specifically, FIG. 5 is a diagram schematically illustrating a situation in which an operator 201 as the user performs surgery on a head of a patient 202 as an observed body. The operator 201 wears glasses 301 for a three-dimensional image, views the three-dimensional image displayed by the display apparatus 4, grips and moves the microscope unit 7 to a desired position while pressing the arm operation switch 73 of the microscope unit 7, determines an imaging visual field of the microscope unit 7, and releases his/her finger from the arm operation switch 73. Accordingly, the electromagnetic brakes of the first joint part 11 to the sixth joint part 16 operate, and the imaging visual field of the microscope unit 7 is fixed. Thereafter, the operator 201 adjusts the enlargement magnification and the focal length to the observed body. The display apparatus 4 displays the three-dimensional image, and therefore, the operator 201 is able to recognize a surgical site three-dimensionally via the three-dimensional image.

To allow the operator 201 to easily grip the microscope unit 7 and to prevent disturbance of the field of view when the operator 201 views the display apparatus 4 or the surgical site of the patient 202, it is more preferable to set an outer diameter of the tubular part 71 to about 40 to 70 millimeters (mm), set a distance between a focal position of the microscope unit 7 and a lower end of the microscope unit 7 to about 150 to 600 mm, and set a total height of the microscope unit 7 and the first joint part 11 to about 100 to 220 mm, for example.

In the present embodiment as described above, the cable group 81 as a bundle and the light guide cables 82 and 83 as a bundle are bound by the binding units 91 to 93 on the path (second section) which is located outside the section where the cables are arranged along the first axis $O_1$ and in which the cables extend in directions different from the first axis $O_1$, so that a cable length between the first axis $O_1$ and the binding units may be reliably set to a length corresponding to the amount of displacement that occurs when the cables are pulled due to rotation of the microscope unit 7 about the first axis $O_1$. Furthermore, in the embodiment, the sizes of the openings of the through holes 111a and 211a through which the cable group 81 and the light guide cables 82 and 83 penetrate are set to be larger than the length of the bundle of the cable group 81 and the light guide cables 82 and 83 in the circle direction, so that it is possible to ensure a large space for preventing interference in the first joint part 11 with respect to the displacement that occurs when the cables are pulled. According to the embodiment, it is possible to prevent interference of the cables at the time of rotation of the microscope unit.

Moreover, according to the present embodiment, the binding units 91 and 92 bind portions that extend in directions different from the first axis $O_1$ in the cable group 81 and the light guide cables 82 and 83, so that it is possible to prevent the cable group 81 and the light guide cables 82 and 83 from extending in the first axis $O_1$ due to the binding, and it is possible to reduce a height of the cable group in the direction of the first axis $O_1$. Consequently, it is possible to reduce a cable arrangement space in the direction of the first axis $O_1$, and prevent an increase in the size of the first joint part 11 in the direction of the first axis $O_1$. By preventing an increase in the size of the first joint part 11 in the direction of the first axis $O_1$, it is possible to prevent the first joint part 11 from disturbing the field of view of the user.

Furthermore, according to the present embodiment, the cable group 81 and the light guide cables 82 and 83 are arranged inside the support unit 6, so that the field of view of the user is not disturbed as compared to a case in which the cable group 81 and the light guide cables 82 and 83 are arranged outside the support unit 6, and it is possible to fully ensure the field of view of the user. Meanwhile, in the present embodiment, to maintain a sterile state of the observation apparatus 2, it may be possible to arrange a sterile drape that covers a front side of the observation apparatus 2. When the sterile drape is adopted, and if the cable group 81 and the light guide cables 82 and 83 are exposed to the outside of the support unit 6, an outer diameter of each of the units of the observation apparatus 2 is further increased and a visual field between the user and the display apparatus 4 is disturbed, so that the user may have difficulty in observation. In contrast, in the present embodiment, the cable group 81 and the light guide cables 82 and 83 are arranged inside the support unit 6, so that even when the sterile drape is adopted, it is possible to fully ensure the visual field of the user.

Moreover, according to the present embodiment, the user grips the microscope unit 7 in the user's hand, so that the user is able to intuitively recognize a direction of the optical axis of the optical system 721 or the imaging visual field of the microscope unit 7, and is able to easily move the microscope unit 7 to a desired position. This is one of significant advantageous effects as compared to a case in which, as in a known surgical microscope, a grip on which a switch for inputting an operation signal is separated from a direction of an optical axis of an optical system and it is difficult to intuitively recognize the direction of the optical axis.

Furthermore, according to the present embodiment, the support unit 6 is constructed by connecting the plurality of arm parts and joint parts, so that it is possible to realize various kinds of motions of the microscope unit 7 with a simple structure, as compared to a known link mechanism.

While the embodiment has been described above, the present disclosure is not limited to the embodiment as described above. For example, it is sufficient that the support unit 6 includes at least a single set of two arm parts and a joint part that connects one of the two arm parts to the other one of the two arm parts in a rotatable manner.

While the example has been described in the above embodiment in which the cables are bound at positions that do not cross the first axis $O_1$ on both sides across the hollow part 76a (a portion crossing the first axis $O_1$), it is possible to achieve the same effects as described above as long as the cables are bound at the position that does not cross the first axis $O_1$ at least on one side. For example, it may be possible to bind the cables by the binding unit 93 that does not cross the first axis $O_1$ on the first arm part 21 side, and bind the cables at a position that crosses the first axis $O_1$ on the microscope unit 7 side, e.g., at the position in the vicinity of the opening of the hollow part 76a and at which the cables extend in the direction of the first axis $O_1$.

Furthermore, while the example has been described in the above embodiment in which the binding unit 93 is arranged in the first arm part 21, the binding unit 93 may be arranged in the first joint part 11 as long as it is possible to ensure the second section and a cable length corresponding to the pulling.

Moreover, while the example has been described in the above embodiment in which the binding unit 93 collectively binds the cable group 81 and the light guide cables 82 and 83, it may be possible bind each of the cable group 81 and the light guide cables 82 and 83 by a different binding unit. In this case, it is possible to achieve the same effects as described above if at least the binding unit that binds the light guide cables meets the above-described condition, such as an arrangement position of the binding unit.

Furthermore, while the example has been described in the above embodiment in which the plurality of coaxial cable wires (the cable group 81) and the plurality of light guide cables are provided, it is sufficient to arrange at least a single coaxial cable wire and a single light guide.

Moreover, while the example has been described in the above embodiment in which the cable group is bound in the first joint part 11, the binding may be adopted in a portion, such as the third joint part 13 and the sixth joint part 16, in which a cable extending direction and a rotation axis of the joint (the third axis O3 and the sixth axis O6) are parallel to each other.

Furthermore, the imaging unit 72 may be configured to include one imaging sensor or include three or more imaging sensors. If the imaging unit 72 includes only a single imaging sensor, the display apparatus 4 displays a two-dimensional image.

Moreover, the operation input unit arranged in the tubular part 71 is not limited to the example as described above. For example, it may be possible to separately arrange an optical unit for changing the enlargement magnification and an operating unit for changing the focal distance to the observed body.

Furthermore, the medical observation apparatus may be arranged by being hang down from the ceiling of an installation place.

As described above, the present disclosure may include various embodiments without departing from the scope of the general concepts as defined by the appended claims.

According to the present disclosure, it is possible to reduce a size of a microscope unit and prevent interference of a cable at the time of rotation of the microscope unit.

Although the disclosure has been described with respect to the specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation system comprising:
   a microscope;
   a support including
      a first joint configured to hold the microscope such that the microscope is rotatable about a first axis parallel to an optical axis of the microscope, the first joint including a hollow shaft that extends along the first axis; and
      a first arm configured to hold the first joint and extend in a direction different from a direction of the optical axis of the microscope;
   a light guide cable inserted in the support and configured to guide illumination light to the microscope;
   a first binder in the first arm, the first binder configured to bind the light guide cable; and
   a second binder configured to bind the light guide cable, wherein
   at least a part of the light guide cable is arranged along the first axis in the hollow shaft in a first section,
   the light guide cable extends in a first direction different from the first axis in a second section,
   the light guide cable extends in a second direction different from the first axis in a third section located opposite to the second section across the first section,
   the first binder is configured to bind the light guide cable in the second section,
   the second binder is configured to bind the light guide cable in the third section, and
   the light guide cable is bendable between the hollow shaft and the first binder such that the first direction ranges between an acute angle relative to the first axis and an obtuse angle relative to the first axis during rotation of the first joint.

2. The medical observation system according to claim 1, wherein
   the microscope is configured to capture an image of a micro region of an observed body in an enlarged manner and output an imaging signal,
   the medical observation system further comprising:
      a controller configured to perform signal processing on the imaging signal output by the microscope and generate image data to be displayed; and
      a signal cable configured to connect the microscope and the controller, the signal cable being inserted in the support, and configured to transmit the imaging signal, and
   the first binder is configured to bind the signal cable and the light guide cable in the second section.

3. The medical observation system according to claim 2, further comprising:
   a plurality of the light guide cables; and
   a plurality of the signal cables, wherein
   the first binder is configured to bind the plurality of light guide cables and the plurality of signal cables in the second section.

4. The medical observation system according to claim 3, further comprising:
   a third binder configured to bind the plurality of signal cables in the third section.

5. The medical observation system according to claim 4, wherein
   a diameter of the light guide cable is larger than a diameter of the signal cable, and
   a length between the first binder on an end side of the light guide cable and the second binder on a different end side of the light guide cable is longer than a length between the first binder on an end side of the signal cable and the third binder on a different end side of the signal cable.

6. The medical observation system according to claim 1, wherein
   the second section includes the first arm, and
   the first binder is arranged on the first arm.

7. The medical observation system according to claim 1, wherein
   the first binder is arranged at a position separated from the first axis by a distance that is longer than a half of an inner diameter of the hollow shaft.

8. The medical observation system according to claim 1, wherein the first joint is configured to rotate the microscope by 360° or larger.

9. The medical observation system according to claim 1, wherein
   a distance of the light guide cable from the first binder to the second binder is equal to or larger than four times of an inner diameter of the hollow shaft.

10. The medical observation system according to claim 6, wherein an opening in the first joint and an opening in the first arm through which the light guide cable extends is larger than a displacement of the light guide cable.

11. The medical observation system according to claim 1, wherein the first direction and the second direction are not parallel to the first axis.

12. The medical observation system according to claim 1, wherein the second direction is perpendicular to the first axis.

13. The medical observation system according to claim 1, wherein the support includes space for the light guide to be bendable between the acute angle and the obtuse angle.

* * * * *